United States Patent
Lebofsky et al.

(10) Patent No.: US 10,730,030 B2
(45) Date of Patent: Aug. 4, 2020

(54) MULTIPLE BEADS PER DROPLET RESOLUTION

(71) Applicant: Bio-Rad Laboratories, Inc., Hercules, CA (US)

(72) Inventors: Ronald Lebofsky, Antony (FR); Nicholas Heredia, Mountain House, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/400,756

(22) Filed: Jan. 6, 2017

(65) Prior Publication Data

US 2017/0232417 A1 Aug. 17, 2017

Related U.S. Application Data

(60) Provisional application No. 62/276,592, filed on Jan. 8, 2016.

(51) Int. Cl.
*B01J 19/00* (2006.01)
*C12Q 1/6806* (2018.01)

(52) U.S. Cl.
CPC ........ *B01J 19/0046* (2013.01); *C12Q 1/6806* (2013.01); *B01J 2219/00547* (2013.01); *B01J 2219/00596* (2013.01); *B01J 2219/00722* (2013.01)

(58) Field of Classification Search
None
See application file for complete search history.

(56) References Cited

U.S. PATENT DOCUMENTS

| | | | | |
|---|---|---|---|---|
| 2010/0048410 A1* | 2/2010 | Shenderov | ....... | G01N 33/54326 506/7 |
| 2012/0220494 A1* | 8/2012 | Samuels | ............ | C12N 15/1075 506/16 |
| 2013/0274117 A1* | 10/2013 | Church | ................ | C12Q 1/6869 506/4 |
| 2013/0323732 A1 | 12/2013 | Anderson et al. | | |
| 2014/0274786 A1 | 9/2014 | McCoy et al. | | |
| 2014/0378349 A1* | 12/2014 | Hindson | .............. | C12Q 1/6806 506/26 |
| 2015/0379196 A1 | 12/2015 | Schnall-Levin et al. | | |

FOREIGN PATENT DOCUMENTS

| | | | | |
|---|---|---|---|---|
| WO | WO-2012019765 A1 * | 2/2012 | ......... | C12N 15/1065 |
| WO | 2012/061832 A1 | 5/2012 | | |
| WO | 2015/200541 A1 | 12/2015 | | |

OTHER PUBLICATIONS

The International Search Report and Written Opinion from Application No. PCT/US2017/12618, dated Mar. 30, 2017.
Extended European Search Report from EP Application 17736475.9 dated Aug. 9, 2018; 8 pages.
Macosko, E.Z. et al.; "Highly Parallel Genome-wide Expression Profiling of Individual Cells Using Nanoliter Droplets"; *CELL*; vol. 161, No. 5; May 21, 2015; pp. 1202-1214.
Shembekar, N. et al.; "Droplet-based microfluidics in drug discovery, transcriptomics and high-throughput molecular genetics"; *Lab on a Chip*; vol. 16, No. 8; Jan. 1, 2016; pp. 1314-1331.

* cited by examiner

*Primary Examiner* — Tracy Vivlemore
*Assistant Examiner* — Sahana S Kaup
(74) *Attorney, Agent, or Firm* — Kilpatrick Townsend and Stockton LLP

(57) ABSTRACT

Methods of generating a nucleic acid signature for identifying particles associated in a partition are provided. In one aspect, the method comprises: partitioning a sample into a plurality of partitions comprising a particle comprising a solid support surface, the solid support surface having a plurality of oligonucleotide primers conjugated thereon, wherein the oligonucleotide primers comprise a barcode sequence, and wherein the partitions have 0, 1, or more than 1 particles per partition; providing in a partition a substrate comprising a barcode sequence or repeating clonal barcode sequences; and in the partition, associating a first particle conjugated to oligonucleotide primers comprising a first barcode sequence and a second particle conjugated to oligonucleotide primers comprising a second barcode sequence to a barcode sequence from the substrate, thereby generating a nucleic acid signature for the particles in the partition.

18 Claims, 5 Drawing Sheets

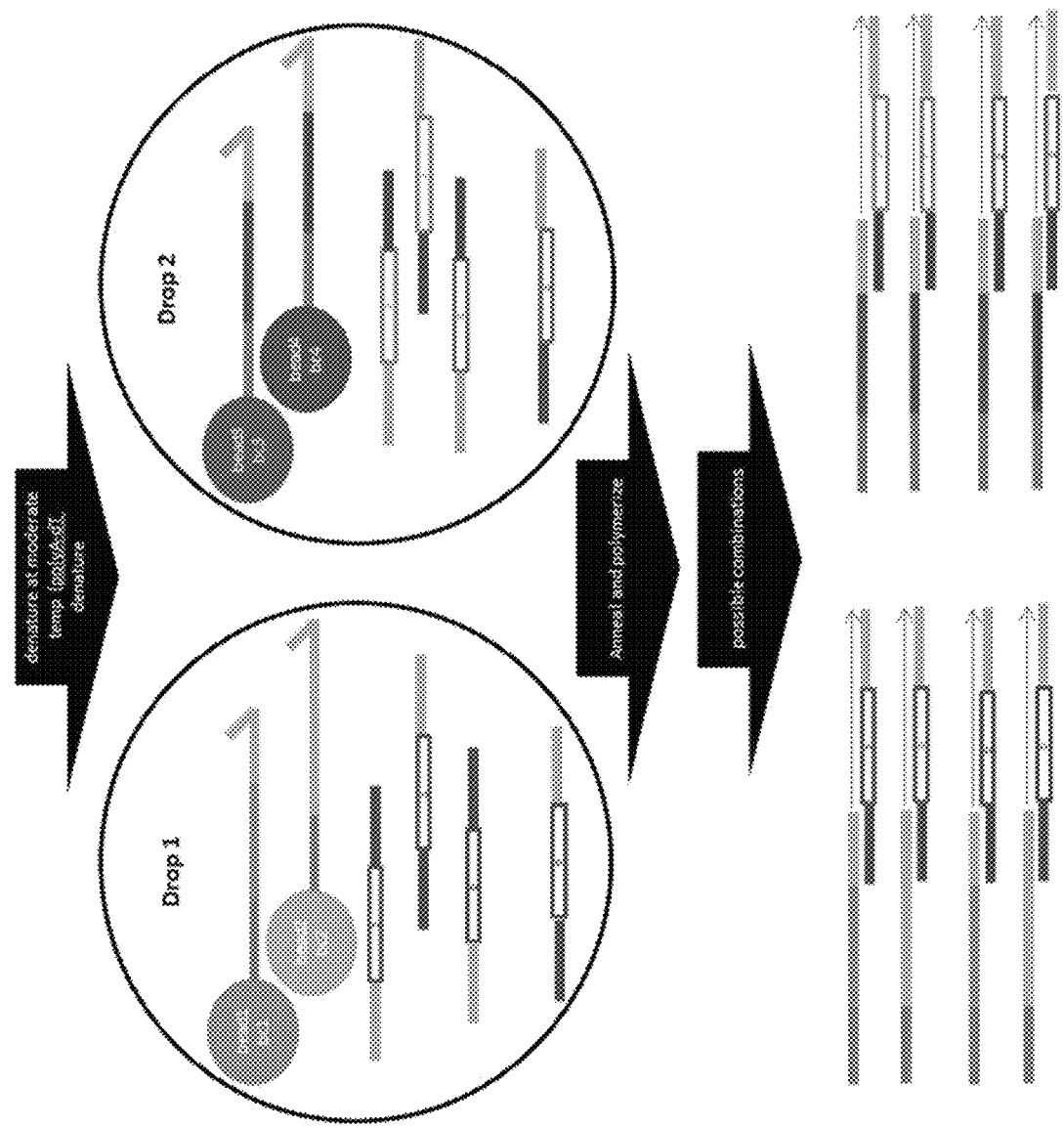

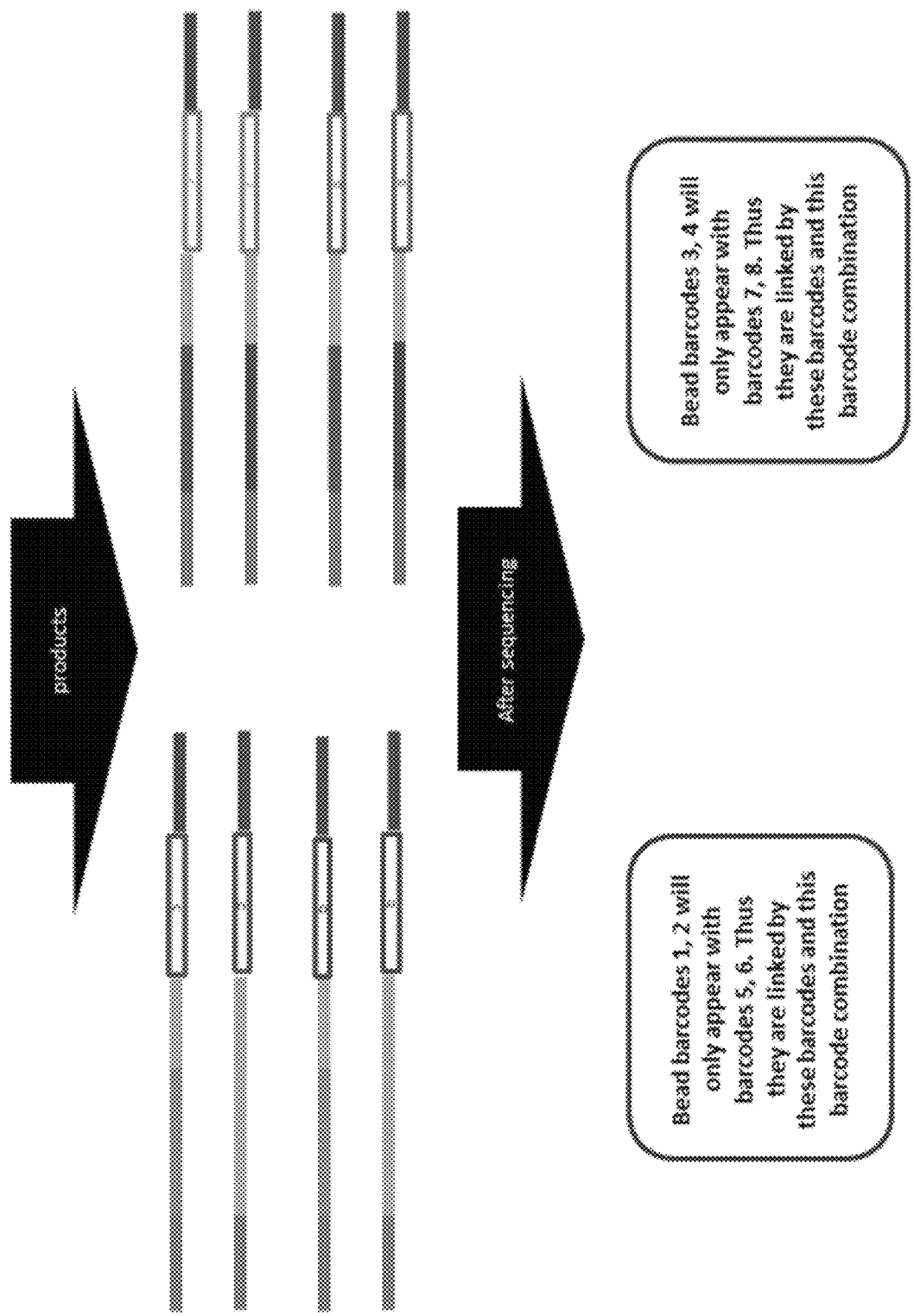

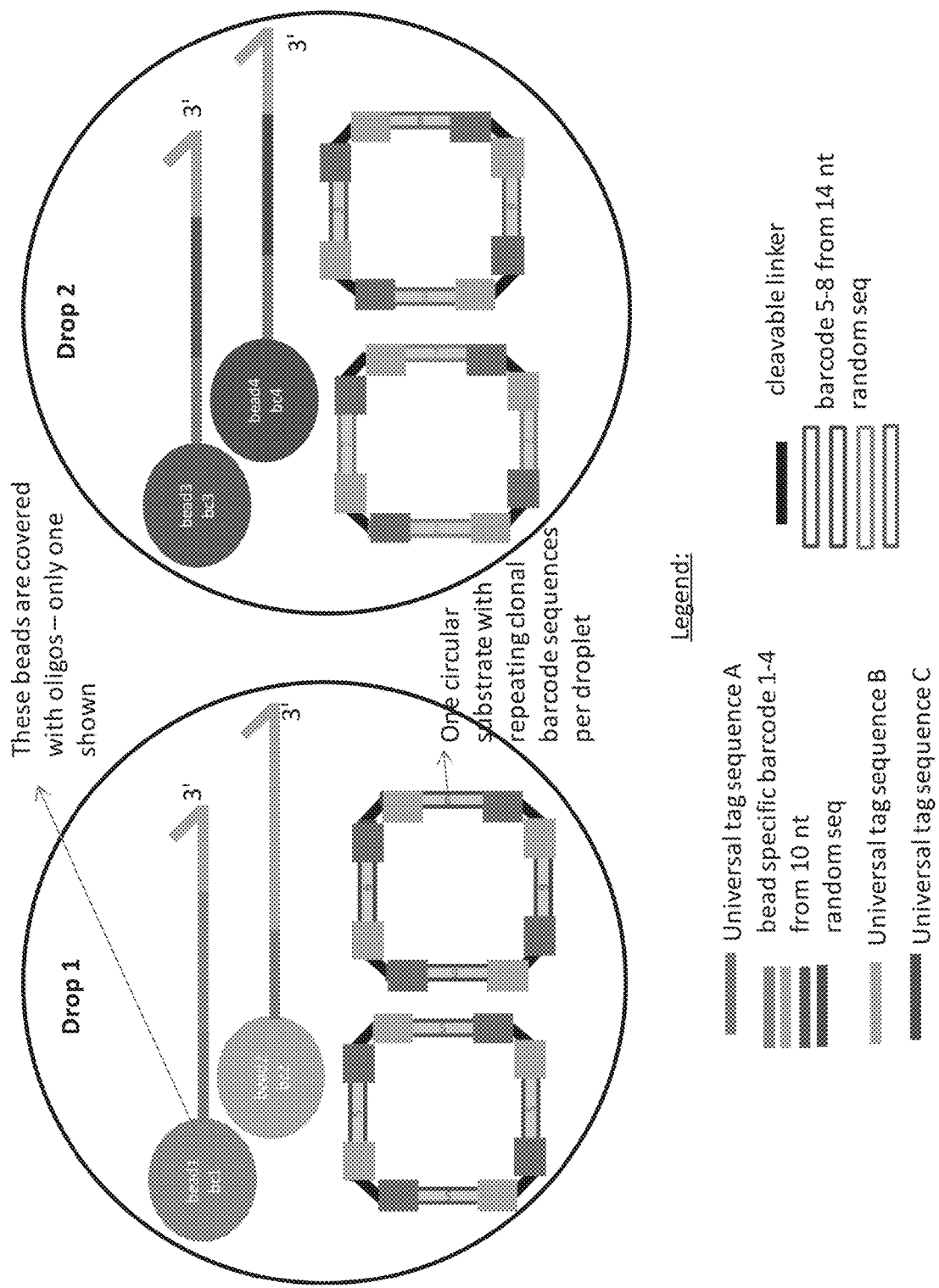

MULTIPLE BEADS PER DROPLET RESOLUTION

CROSS-REFERENCE TO RELATED APPLICATIONS

This application claims priority to U.S. Provisional Application No. 62/276,592, filed Jan. 8, 2016, the content of which is incorporated herein in its entirety.

BACKGROUND OF THE INVENTION

Beads conjugated to oligonucleotides are used in microfluidic detection applications such as high-throughput sequencing. In order to uniquely identify each partition, the beads can be labeled with unique barcode sequences. However, in order to ensure that partitions have only one bead and thus are uniquely labeled by the barcode, bead concentrations are typically adjusted so that only about 1 out of 10 partitions are occupied by a bead. This results in about 90% dead volume in the partitions, and increases the amount of sample and reagents that is needed for detection of samples.

BRIEF SUMMARY OF THE INVENTION

In one aspect, methods of generating a nucleic acid signature for identifying particles associated in a partition are provided. In some embodiments, the method comprises:
(a) partitioning a sample into a plurality of partitions comprising a particle comprising a solid support surface, the solid support surface having a plurality of oligonucleotide primers conjugated thereon, wherein the oligonucleotide primers comprise a barcode sequence and wherein at least a majority of the plurality of oligonucleotide primers conjugated to a solid support surface comprise the same barcode sequence, and wherein the partitions have 0, 1, or more than 1 particles per partition;
(b) providing in a partition a substrate comprising a barcode sequence or repeating clonal barcode sequences; and
(c) in the partition, associating a first particle conjugated to oligonucleotide primers comprising a first barcode sequence and a second particle conjugated to oligonucleotide primers comprising a second barcode sequence to a barcode sequence from the substrate; thereby generating a nucleic acid signature for the particles in the partition.

In some embodiments, the providing step comprises releasing the barcode sequence or the repeating clonal barcode sequences from the substrate. In some embodiments, the substrate comprising repeating clonal barcode sequences comprises tandem repeating clonal barcode sequences that are separated by a cleavable linker. In some embodiments, the releasing step comprises cleaving the substrate at the cleavable linker. In some embodiments, the cleavable linker is a restriction enzyme recognition site, a uridine incorporated site, or a photocleavable nucleotide.

In some embodiments, the substrate comprising the barcode sequence or repeating clonal barcode sequences is a droplet encapsulating the repeating clonal barcode sequences, and the providing step comprises releasing the barcode sequence or the repeating clonal barcode sequences from the substrate. In some embodiments, the releasing step comprises breaking the droplet.

In some embodiments, the substrate barcode sequence or repeating clonal barcode sequences comprise DNA, RNA, or a DNA/RNA hybrid. In some embodiments, the substrate barcode sequence or repeating clonal barcode sequences are single-stranded (e.g., single-stranded DNA or RNA). In some embodiments, the substrate barcode sequence or repeating clonal barcode sequences are double-stranded (e.g., double-stranded DNA, RNA, or DNA/RNA hybrid). In some embodiments, the substrate barcode sequence is a contiguity preserved tagmented polynucleotide sequence.

In some embodiments, the substrate comprises repeating clonal barcode sequences. In some embodiments, the substrate comprising the repeating clonal barcode sequences is a hairpin molecule. In some embodiments, the substrate comprising the repeating clonal barcode sequences is a linear polynucleotide substrate. In some embodiments, the substrate comprising the repeating clonal barcode sequences is a circular polynucleotide substrate. In some embodiments, the circular polynucleotide substrate is a plasmid, a DNA nanoball, or a multiple displacement amplified branched substrate.

In some embodiments, the barcode sequence or repeating barcode sequence of the substrate has a length of at least 6 nucleotides. In some embodiments, the repeating clonal barcode sequences comprise at least 2, at least 5, at least 10, at least 50, or at least 100 repeats of the clonal barcode sequence.

In some embodiments, the substrate comprises a single barcode sequence. In some embodiments, the associating step comprises (1) annealing an oligonucleotide primer of the first particle to the substrate barcode sequence and extending the annealed product with a polymerase, and (2) annealing an oligonucleotide primer of the second particle to the substrate barcode sequence and extending the annealed product with the polymerase.

In some embodiments, the providing step comprises providing in a partition a plurality of substrates comprising a barcode sequence or repeating clonal barcode sequences, wherein the plurality of substrates comprise distinguishable barcode sequences. In some embodiments, the providing step comprises providing at least 10, at least 20, at least 30, at least 40, at least 50, at least 100, or at least 200 substrates comprising a barcode sequence or repeating barcode sequence.

In some embodiments, the partitions have an average of at least about 0.5, 0.6, 0.7, 0.8, 0.9, 1, 1.5, 2, 2.5, 3 or more particles per partition. In some embodiments, the partitions are droplets. In some embodiments, the partitions have an average of about 1 particle per partition. In some embodiments, the partitions have an average of about 2 particles per partition. In some embodiments, the partitions have an average of about 3 particles per partition.

In some embodiments, the associating step comprises associating (1) the first particle conjugated to oligonucleotide primers comprising the first barcode sequence with a first substrate barcode sequence, and (2) the second particle conjugated to oligonucleotide primers comprising the second barcode sequence with a second substrate barcode sequence. In some embodiments, the associating step the associating step comprises annealing the first substrate barcode sequence to an oligonucleotide primer of the first particle and the second substrate barcode sequence to an oligonucleotide primer of the second particle and extending the annealed products with a polymerase.

In some embodiments, the associating step comprises at least 1 cycle of annealing and extension. In some embodiments, the associating step comprises at least 5, at least 10, at least 15, at least 20, at least 25, at least 30, at least 35, or at least 40 cycles of annealing and extension.

In some embodiments, the first substrate barcode sequence and the second substrate barcode sequence are from different substrates. In some embodiment, the first substrate barcode sequence and the second substrate barcode sequence are from the same substrate.

In some embodiments, the associating step comprises ligating a substrate barcode sequence to both an oligonucleotide primer of the first particle and an oligonucleotide primer of the second particle.

In some embodiments, the sample comprises a target nucleic acid. In some embodiments, the sample comprising a target nucleic acid comprises a cell containing the target nucleic acid.

In another aspect, a plurality of partitions generated according to the methods described herein are provided.

In another aspect, partition libraries are provided. In some embodiments, the partition library comprises two or more partitions, wherein at least some partitions comprise at least a first particle conjugated to oligonucleotide primers comprising a first barcode sequence and a second particle conjugated to oligonucleotide primers comprising a second barcode sequence, and further comprise a substrate comprising a barcode sequence or repeating clonal barcode sequences.

In some embodiments, the substrate comprises a single barcode sequence. In some embodiments, the substrate comprises repeating clonal barcode sequences. In some embodiments, the substrate comprising the repeating clonal barcode sequences comprises tandem repeating clonal barcode sequences that are separated by a cleavable linker. In some embodiments, the substrate comprising the tandem repeating clonal barcode sequences is a hairpin molecule. In some embodiments, the substrate comprising the tandem repeating clonal barcode sequences is a linear polynucleotide substrate. In some embodiments, the substrate comprising the tandem repeating clonal barcode sequences is a circular polynucleotide substrate. In some embodiments, the substrate comprising the repeating clonal barcode sequences is a droplet encapsulating the repeating clonal barcode sequences.

In some embodiments, the first substrate barcode sequence and the second substrate barcode sequence are distinguishable sequences. In some embodiments, the first substrate barcode sequence and the second substrate barcode sequence are identical sequences.

In some embodiments, the partition library comprises a plurality of substrates comprising a barcode sequence or repeating clonal barcode sequences, wherein the plurality of substrates comprise distinguishable barcode sequences.

In some embodiments, the partition library comprises two or more partitions, wherein at least some partitions comprise at least a first particle conjugated to oligonucleotide primers comprising a first barcode sequence and a second particle conjugated to oligonucleotide primers comprising a second barcode sequence, and further comprise at least one substrate barcode sequence associated with the first particle and the second particle. In some embodiments, at least some partitions comprise a first substrate barcode sequence associated with the first particle conjugated to oligonucleotide primers comprising the first barcode sequence and a second substrate barcode sequence associated with the second particle conjugated to oligonucleotide primers comprising the second barcode sequence. In some embodiments, the first substrate barcode sequence and the second substrate barcode sequence are distinguishable sequences. In some embodiments, the first substrate barcode sequence and the second substrate barcode sequence are identical sequences. In some embodiments, at least some partitions comprise a substrate barcode sequence ligated to both an oligonucleotide primer of the first particle and to an oligonucleotide primer of the second particle.

In some embodiments, a partition library comprises at least 500, at least 1000, at least 10,000, at least 50,000, or at least 100,000 partitions. In some embodiments, the partitions comprise droplets. In some embodiments, the partitions have an average of at least about 0.5, 0.6, 0.7, 0.8, 0.9, 1, 1.5, 2, 2.5, 3 or more particles per partition.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, analytical chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document.

The term "amplification reaction" refers to any in vitro method for multiplying the copies of a target sequence of nucleic acid in a linear or exponential manner. Such methods include, but are not limited to, polymerase chain reaction (PCR); DNA ligase chain reaction (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3 SR); single-primer isothermal amplification (SPIA), loop mediated isothermal amplification (LAMP), strand displacement amplification (SDA); multiple displacement amplification (MDA); rolling circle amplification (RCA); as well as others known to those of skill in the art. See, e.g., Fakruddin et al., *J. Pharm Bioallied Sci.* 2013 5(4):245-252.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths. In some embodiments, a primer is less than 50 nucleotides in length, e.g., from about 10 to about 40, from about 15 to about 40, or from about 15 to about 30 nucleotides in length. The length and sequences of primers for use in an amplification reaction (e.g., PCR) can be designed based on principles known to those of skill in the art; see, e.g., PCR Protocols: A Guide to Methods and Applications, Innis et al., eds, 1990. In some embodiments, a primer comprises one or more modified or non-natural nucleotide bases. In some embodiments, a primer comprises a label (e.g., a detectable label).

A nucleic acid, or portion thereof, "hybridizes" to another nucleic acid under conditions such that non-specific hybridization is minimal at a defined temperature in a physiological buffer. In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C.

As used herein, "nucleic acid" refers to DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

As used herein, the term "partitioning" or "partitioned" refers to separating a sample into a plurality of portions, or "partitions." Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used herein, a "barcode" is a short nucleotide sequence (e.g., at least about 4, 6, 8, 10, 12, or 14 nucleotides long) that identifies a molecule to which it is conjugated. In some embodiments, a barcode is used to identify molecules in a partition. Such a partition-specific barcode should be unique for that partition as compared to barcodes present in other partitions. For example, partitions containing target RNA from single cells can subject to reverse transcription conditions using primers that contain a different partition-specific barcode sequence in each partition, thus incorporating a copy of a unique "cellular barcode" into the reverse transcribed nucleic acids of each partition. Thus, nucleic acid from each cell can be distinguished from nucleic acid of other cells due to the unique "cellular barcode." In some embodiments, a barcode is present on oligonucleotides conjugated to a particle, wherein the "particle barcode" is shared by (e.g., identical or substantially identical amongst) all, or substantially all, of the oligonucleotides conjugated to that particle.

In some embodiments, a barcode is provided in a substrate. In some embodiments, a substrate comprises a single barcode sequence. In some embodiments, a substrate comprises repeating clonal barcode sequences. As used herein, a "substrate comprising repeating clonal barcode sequences" refers to a composition that contains a plurality of identical barcode sequences that are physically connected to each other (e.g., in a hairpin molecule, a linear nucleic acid polymer, or a circular nucleic acid polymer as tandem repeating barcode sequences separated by a cleavable linker between each repeating sequence) or that are sequestered from other components when delivered to a partition (e.g., encapsulated within a droplet that is delivered to a partition). In some embodiments, individual barcode sequences are released from the substrate or released from a repeating clonal barcode sequence (e.g., released from the hairpin, linear nucleic acid polymer, or circular nucleic acid polymer by cleaving the polymer at the cleavable linkers, or released from the droplet by breaking the droplet) in a partition, and are associated with a particle in the partition, for example, by annealing the clonal barcode sequence to an oligonucleotide on the partition or by ligating the clonal barcode sequence to an oligonucleotide on the partition.

As used herein, the term "nucleic acid signature" refers to a unique combination of multiple distinguishable barcodes that is associated with a partition or a combination of particles within a partition. In some embodiments, a nucleic acid signature is used to identify a partition associated with a target nucleic acid (e.g., in a sequencing read, to identify the partition from which a sequenced target nucleic acid originated).

BRIEF DESCRIPTION OF THE DRAWINGS

FIG. 1A-C. Schematic depicting an exemplary process of generating a nucleic acid signature for particles in partitions. (A) A first partition ("Drop 1") comprises two particles ("bead1" and "bead2") with oligonucleotides conjugated to the particles, each particle having a distinguishable barcode on its oligonucleotides ("bc1" and "bc2," respectively). The first partition further comprises two substrates comprising repeating clonal barcode sequences in the form of hairpin oligos, each substrate having a distinguishable barcode (barcode "5" in red, and barcode "6" in purple). A second partition ("Drop 2") comprises two particles ("bead3" and "bead4") with oligonucleotides conjugated to the particles, each particle having a distinguishable barcode ("bc3" and "bc4," respectively). The second partition further comprises two substrates comprising repeating clonal barcode sequences in the form of hairpin oligos, each substrate having a distinguishable barcode (barcode "7" in blue, and barcode "8" in green). Each partition further comprises one target molecule per partition. The cleavable linkers in the hairpin oligos are cleaved, releasing the individual clonal barcode sequences in the partition. (B) The partitions are subjected to denaturation conditions that denature the double-stranded clonal barcode sequences into single-stranded clonal barcode sequences. After an annealing and extension reaction, different combinations of clonal barcode sequences associated with particle-conjugated oligonucleotides are possible in each partition. (C) The combinations of the clonal barcode associated with particle-conjugated oligonucleotides yield a nucleic acid signature for each partition. For Drop 1, bead barcodes 1 and 2 will only appear with clonal barcode sequences 5 and 6. For Drop 2, bead barcodes 3 and 4 will only appear with clonal barcode sequences 7 and 8. In sequencing reads, the presence of a nucleic acid signature associated with a particular partition will indicate the partition from which a target molecule originated.

FIG. 2. Substrates comprising repeating clonal barcode sequences can be circular substrates, including single stranded nucleic acid polymers (RNA, DNA, or a mixture thereof) and double stranded nucleic acid polymers (RNA, DNA, or a mixture thereof). The oligonucleotides conjugated to the particles and the substrate barcode sequences comprise universal tag sequences (tag B, tag C) for hybridizing the substrate barcode sequences to the particle-conjugated oligonucleotides.

DETAILED DESCRIPTION OF THE INVENTION

I. Introduction

Figure 1A:
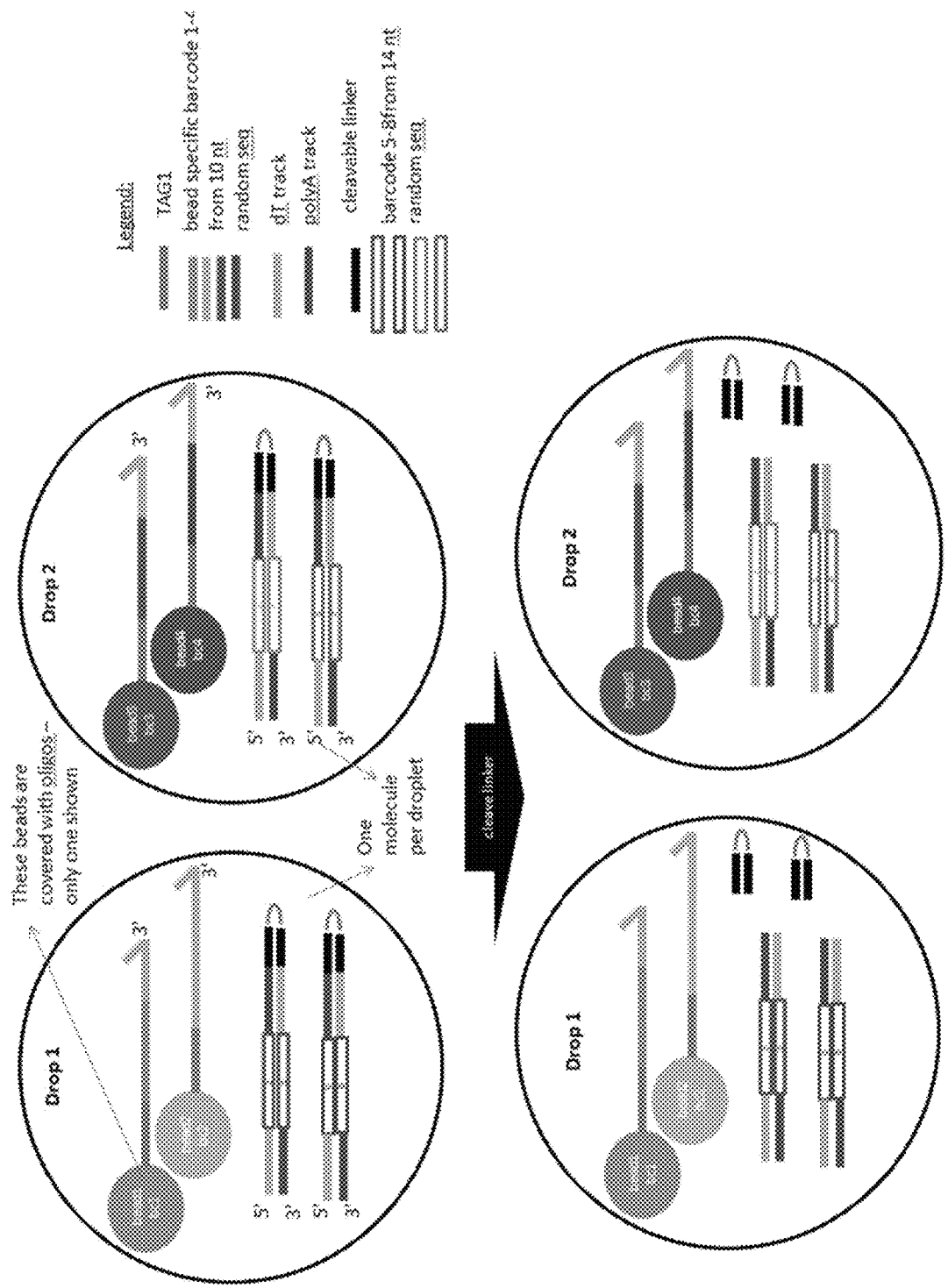

Described herein are methods, compositions, and kits for generating a nucleic acid signature for identifying particles that are associated with each other in a partition. In a partition comprising two or more particles conjugated to barcode sequence-containing oligonucleotide primers (e.g., partitions comprising two particles or partitions comprising three particles), one or more additional barcode sequences are introduced into the partition that are distinct from the barcodes of the oligonucleotide primers conjugated to the particles. In some embodiments, the additional barcode sequences are introduced into a partition in a substrate. The substrate barcode sequences are associated with the oligonucleotide primers (e.g., in annealing and extension reactions, ligation, or amplification reactions) to generate a combination of barcode sequences that is unique to the particles in that partition. This unique combination of barcodes for the particles in a partition is a "nucleic acid signature" that identifies the particles as originating from a specific partition.

Nucleic acid signatures for partitions can be used, e.g., for deconvoluting data from a pool of partitions. For example, in some embodiments, the contents of multiple partitions are pooled for detection (e.g., by sequencing), and the nucleic acid signature can be used to deconvolute the sequencing data in order to identify the specific partition from which a target nucleic acid originated.

The methods, compositions, kits, and partition libraries described herein can be used, e.g., for increasing the rate of occupancy for partitions loaded with particles. As described herein, the use of two or three particles per partition on average increases particle occupancy from about 10% to about 85% or 95%, thereby drastically minimizing the dead volume of partitions and improving the efficiency of partition-based reactions.

II. Methods of Generating a Nucleic Acid Signatures for Particles in a Partition In one aspect, methods of generating a nucleic acid signature for identifying particles associated in a partition are provided. In some embodiments, the method comprises:
(a) partitioning a sample into a plurality of partitions comprising a particle comprising a solid support surface, the solid support surface having a plurality of oligonucleotide primers conjugated thereon, wherein the oligonucleotide primers comprise a barcode sequence and wherein at least a majority of the plurality of oligonucleotide primers conjugated to a solid support surface comprise the same barcode sequence, and wherein the partitions have 0, 1, or more than 1 particles per partition;
(b) providing in a partition a substrate comprising a barcode sequence or repeating clonal barcode sequences; and
(c) in the partition, associating a first particle conjugated to oligonucleotide primers comprising a first barcode sequence and a second particle conjugated to oligonucleotide primers comprising a second barcode sequence to a clonal barcode sequence;
thereby generating a nucleic acid signature for the particles in the partition.

In some embodiments, the sample to be partitioned comprises one or more target nucleic acids. In some embodiments, the sample to be partitioned comprises one or more target nucleic acids and further comprises particles conjugated to the oligonucleotide primers and/or substrates comprising repeating clonal barcode sequences.

Samples

In some embodiments, the method comprises partitioning a sample comprising one or more target nucleic acids into a plurality of partitions. In some embodiments, the sample comprising target nucleic acids comprises DNA, RNA, or a combination or hybrid thereof. In some embodiments, the sample comprising target nucleic acids comprises genomic DNA or DNA from a subset of a genome (e.g., selected genes that may harbor mutations for a particular population, such as individuals who are predisposed for a particular type of cancer). In some embodiments, the sample comprising target nucleic acids comprises cDNA. In some embodiments, the sample comprising target nucleic acids comprises exome DNA (i.e., a subset of whole genomic DNA enriched for transcribed sequences which contains the set of exons in a genome) or transcriptome DNA (i.e., the set of all mRNA or "transcripts" produced in a cell or population of cells). In some embodiments, the sample comprising target nucleic acids comprises long fragment DNA (e.g., DNA having a length of at least about 300, 400, 500, 600, 700, 800, 1000, or more bases, or base pairs for double-stranded DNA). In some embodiments, the sample comprising target nucleic acids comprises RNA, e.g., mRNA or lncRNA. In some embodiments, the target nucleic acids are double stranded. In some embodiments, the target nucleic acids are single stranded. In some embodiments, the sample comprises target nucleic acids isolated from tissue, cells, or a single-cell sample.

In some embodiments, the sample comprising target nucleic acids is a biological sample. Biological samples can be obtained from any biological organism, e.g., an animal, plant, fungus, pathogen (e.g., bacteria or virus), or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, and transformed cells, stem cells, stool, urine, etc. In some embodiments, the sample is a sample comprising cells. In some embodiments, the sample is a single-cell sample.

In some embodiments, the methods described herein are used for single cell analysis. Accordingly, in some embodiments, target nucleic acids from a single cell are partitioned into a plurality of partitions. In some embodiments, target nucleic acids from a biological sample containing a plurality of cells are extracted and partitioned such that individual partitions contain nucleic acid from less than one, one, or a plurality of cells.

Particles Conjugated to Oligonucleotide Primers

In some embodiments, particles that are conjugated to barcode-labeled oligonucleotide primers are used in the methods, partition libraries, and kits described herein. In some embodiments, the particle comprises a solid support surface having a plurality of oligonucleotide primers conjugated thereon. In some embodiments, the particle comprises at least about 10, 50, 100, 500, 1000, 5000, 10,000, 50,000, 100,000, 500,000, 1,000,000, 5,000,000, 10,000,000 or more oligonucleotide primers conjugated thereto. In some embodiments, the oligonucleotide primers are double stranded. In some embodiments, the oligonucleotide primers are single stranded.

In some embodiments, the oligonucleotide primers comprise a barcode sequence, wherein at least a majority, substantially all, or all of the plurality of oligonucleotide primers conjugated to a solid support surface comprise the same barcode sequence. In some embodiments, the barcode is a sequence of about 6 to about 20 nucleotides, e.g., about 6-16, about 6-14, about 8-20, about 8-18, about 10-20, about 10-18, or about 12-20 nucleotides. In some embodiments, the barcode is a sequence of at least about 10 nucleotides. In some embodiments, the oligonucleotide primers conjugated to a particular particle comprise a barcode sequence that is the same or substantially the same among the plurality of oligonucleotides on a particle, but unique or substantially unique as compared to the plurality of oligonucleotides on other particles.

In some embodiments, the oligonucleotide primers comprise a "tag" portion. In some embodiments, the tag portion provides a functionality to be used for downstream steps. For example, in some embodiments, the tag portion comprises a universal sequence that is common to all or substantially all oligonucleotide primers on all particles. In some embodiments, the tag portion comprises a primer for use in a downstream amplification step. In some embodiments, the tag portion comprises a sequence or a partial sequence of a sequencing adapter, e.g., a RD1 sequence from the P5 adapter (Illumina), or a sequence complementary to the adapter sequence or portion of the adapter sequence (e.g., RD1 sequence). In some embodiments, the tag portion is at the 5' end of the oligonucleotide primer.

In some embodiments, the oligonucleotide primers comprise a random sequence portion. In some embodiments, the random sequence portion of an oligonucleotide primer is used for hybridizing to a target nucleic acid or a clonal barcode sequence and/or is used as a primer in a downstream primer extension step. In some embodiments, the random sequence portion is a sequence of at least about 5, 10, 15 or more nucleotides, e.g., about 6-8, about 6-10, or about 5-15 nucleotides.

In some embodiments, the oligonucleotide primers comprise a poly-thymine region. In some embodiments, the poly-thymine region comprises from about 15 to about 20, or from about 15 to about 35 thymine nucleotides. In some embodiments, the poly-thymine region is at the 3' end of the oligonucleotide primer.

In some embodiments, the plurality of oligonucleotide primers are conjugated to the solid support surface of the particle at the 5' end of the oligonucleotide primer. In some embodiments, the oligonucleotide primers comprise a barcode sequence portion in the middle portion of the oligonucleotide primer and a 3' end that is available for ligation and/or extension by a polymerase.

Solid supports suitable for attaching oligonucleotides thereto include controlled pore glass (CPG) (available from Glen Research, Sterling, Va.), oxalyl-controlled pore glass (See, e.g., Alul, et al., Nucleic Acids Research 1991, 19, 1527), TentaGel Support—an aminopolyethyleneglycol derivatized support (See, e.g., Wright, et al., Tetrahedron Letters 1993, 34, 3373), polystyrene, Poros—a copolymer of polystyrene/divinylbenzene, or reversibly cross-linked acrylamide. Many other solid supports are commercially available and amenable to use in attaching oligonucleotides thereto.

In some embodiments, a solid support is coated with a material to aid in the attachment of an oligonucleotide primer to the surface. Exemplary surface coatings include, but are not limited to metals such as gold, silver, steel, aluminum, silicon, and copper.

In some embodiments, the solid support is a bead (e.g., silica gel, glass (e.g., controlled pore glass), magnetic bead, plastic, metal, polystyrene, or polymer bead). In some embodiments, the bead has a size of about 1 μm to about 100 μm in diameter. Bead diameters may be selected based on the sizes of the partitions (e.g., the sizes of microfluidic channels or droplets as discussed herein).

Particles comprising oligonucleotides conjugated to a solid support surface, including barcode-labeled oligonucleotides, and methods of making such particles, are known in the art. See, e.g., U.S. Pat. No. 6,133,436; US 2011/0028334; and International Application No. PCT/US2015/037525, incorporated by reference herein.

Substrates Comprising Barcode Sequences

In some embodiments, substrates comprising a barcode sequence or repeating clonal barcode sequences are provided. In some embodiments, a substrate comprises a single barcode sequence (i.e., does not comprise repeating clonal barcode sequences). In some embodiments, the substrate comprising the single barcode sequence is a hairpin molecule. In some embodiments, the substrate comprising the single barcode sequence is a linear polynucleotide substrate. In some embodiments, the substrate comprising the single barcode sequence is a circular polynucleotide substrate. In some embodiments, the substrate comprising the single barcode sequence is encapsulated in a droplet.

In some embodiments, a substrate comprises repeating clonal barcode sequences. As used herein, a "substrate comprising repeating clonal barcode sequences" refers to a composition that contains a plurality of identical "clonal" barcode sequences that are either physically connected to each other (e.g., in a hairpin molecule, in a linear nucleic acid polymer, or in a circular nucleic acid polymer as tandem repeating barcode sequences) or that are sequestered from other components when delivered to a partition (e.g., encapsulated within a droplet that is delivered to a partition). In some embodiments, the clonal barcode sequences are not available to associate with oligonucleotide primers of particles in a partition without first being released from the physical connection or sequestration. In some embodiments, a plurality of substrates (e.g., a plurality of hairpin molecules, linear nucleic acid polymers, circular nucleic acid polymers, or droplets) are delivered to a partition. For example, in some embodiments, a partition comprises at least about 5, 10, 15, 20, 25, 30, 35, 40, 50, 60, 70, 80, 90, 100, 110, 120, 130, 140, 150, 160, 170, 180, 190, 200 or more substrates.

In some embodiments, a substrate barcode sequence has a length of at least 6 nucleotides. In some embodiments, the substrate barcode sequence has a length of at least about 6, 7, 8, 9, 10, 11, 12, 13, 14, 15, 16, 17, 18, 19, 20, 21, 22, 23, 24 or 25 nucleotides. In some embodiments, the substrate barcode sequence has a length of about 6 to about 25 nucleotides.

In some embodiments, the clonal barcode sequences from a particular substrate comprise a region of nucleotide sequence that is a unique identifier sequence for all of the clonal barcode sequences from that substrate, and the clonal barcode sequences further comprise a poly-thymine region and/or a poly-adenine region flanking the region of unique identifier sequence. In some embodiments, a poly-adenine region or poly-thymine comprises from about 15 to about 20, or from about 15 to about 35 thymine nucleotides. In some embodiments, a poly-adenine region of a clonal barcode sequence is used for hybridizing the clonal barcode sequence to an oligonucleotide primer at a poly-thymine region of the oligonucleotide primer. See, e.g., FIG. 1.

In some embodiments, a barcode sequence or clonal barcode sequences from a particular substrate comprise a region of nucleotide sequence that is a unique identifier sequence for all of the clonal barcode sequences from that substrate, and further comprise one or more universal tag sequences. In some embodiments, the universal tag sequence is used for hybridizing the substrate barcode sequence to an oligonucleotide conjugated to a particle.

In some embodiments, a substrate barcode sequence is a contiguity preserved tagmented polynucleotide (e.g., DNA) sequence. In contiguity preserved transposition or tagmentation, a tagmentase or transposase (e.g., Tn5 transposase) is used to modify DNA with adaptor sequences while maintaining contiguity of DNA segments. The DNA can also be labeled or modified with barcode or index sequences. Methods of preparing contiguity preserved tagmented polynucleotide sequences are known. See, e.g., Amini et al., Nature Genetics, 2014, 46:1343-1349; WO 2016/061517; and U.S. Provisional Patent Application No. 62/436,288; each of which is incorporated by reference herein.

In some embodiments, a substrate comprising repeating clonal barcode sequences is a hairpin molecule of tandem repeating clonal barcode sequences, wherein the clonal barcode sequences are identical to each other and wherein the barcode sequences are separated by a cleavable linker between each repeating sequence. In some embodiments, the hairpin molecule comprises at least 2, 3, 4, 5, 6, 7, 8, 9, 10, 15, 20, 25, 30, 35, 40, 50, 60, 70, 80, 90, 100 or more tandem repeating clonal barcode sequences.

In some embodiments, a substrate comprising repeating clonal barcode sequences is a linear nucleic acid polymer of tandem repeating clonal barcode sequences, wherein the clonal barcode sequences are identical to each other and wherein the barcode sequences are separated by a cleavable linker between each repeating sequence. In some embodiments, the linear polymer comprises at least 2, 3, 4, 5, 6, 7, 8, 9, 10, 15, 20, 25, 30, 35, 40, 50, 60, 70, 80, 90, 100 or more tandem repeating clonal barcode sequences. In some embodiments, the linear nucleic acid polymer comprises DNA, RNA, or a hybrid of DNA and RNA. In some embodiments, the linear nucleic acid polymer is double stranded. In some embodiments, the linear nucleic acid polymer is single stranded.

In some embodiments, a substrate comprising repeating clonal barcode sequences is a circular nucleic acid polymer of tandem repeating clonal barcode sequences, wherein the clonal barcode sequences are identical to each other and wherein the barcode sequences are separated by a cleavable linker between each repeating sequence. In some embodiments, the circular polymer comprises at least 2, 3, 4, 5, 6, 7, 8, 9, 10, 15, 20, 25, 30, 35, 40, 50, 60, 70, 80, 90, 100 or more tandem repeating clonal barcode sequences. In some embodiments, the circular polymer is a plasmid. In some embodiments, the circular polymer is a DNA nanoball (i.e., a single stranded DNA molecule that collapses into a spheroid structure due to secondary structures forming at regular intervals). In some embodiments, the circular polymer is a multiple displacement amplified branched substrate. In some embodiments, the circular nucleic acid polymer comprises DNA, RNA, or a hybrid of DNA and RNA. In some embodiments, the circular nucleic acid polymer is double stranded. In some embodiments, the circular nucleic acid polymer is single stranded.

In some embodiments, the substrate comprising the barcode sequence or repeating clonal barcode sequences is a droplet encapsulating the repeating clonal barcode sequences. In some embodiments, the droplet encapsulating the repeating clonal barcode sequences comprises at least 2, 3, 4, 5, 6, 7, 8, 9, 10, 15, 20, 25, 30, 35, 40, 50, 60, 70, 80, 90, 100 or more clonal barcode sequences that are identical to each other. In some embodiments, the droplet comprises an emulsion composition, i.e., a mixture of immiscible fluids (e.g., water and oil). In some embodiments, the droplet is an aqueous droplet that is surrounded by an immiscible carrier fluid (e.g., oil). In some embodiments, the droplet is an oil droplet that is surrounded by an immiscible carrier fluid (e.g., an aqueous solution). In some embodiments, the droplet has a diameter of about 0.001 microns to about 500 microns, e.g., about 0.005 to about 100 microns, or about 0.01 to about 50 microns. The size of the droplet may be selected based on the sizes of the partitions (e.g., the sizes of microfluidic channels or droplets as discussed herein). Methods of generating droplets are described below and are also described, e.g., in published patent applications WO 2011/109546 and WO 2012/061444, the entire content of each of which is incorporated by reference herein.

In some embodiments, wherein the substrate comprising a barcode sequence or repeating clonal barcode sequences is a droplet encapsulating the repeating clonal barcode sequences, the droplet that is within a partition is relatively unstable and can be triggered to release the barcode sequences into the partition without breaking the partition. In some embodiments, factors such as surfactants, oils, osmolarity, or heat lability can affect the ability of a droplet within a partition to release the contents of the droplet into the partition.

Partitioning

In some embodiments, a sample (e.g., a sample comprising target nucleic acids) is partitioned into a plurality of partitions. In some embodiments, the sample comprising target nucleic acids is partitioned such that the partition contains 0, 1, or more than 1 target nucleic acids. In some embodiments, the sample comprising target nucleic acids is partitioned such that, on average, the partitions contain no more than 1 target nucleic acid. In some embodiments, a sample for partitioning further comprises particles conjugated to oligonucleotide primers as described herein. In some embodiments, wherein the sample comprises particles conjugated to oligonucleotide primers, the sample is partitioned such that, on average, a partition contains about one particle. In some embodiments, wherein the sample comprises particles conjugated to oligonucleotide primers, the sample is partitioned such that, on average, a partition contains at least two particles (e.g., such that, on average, a partition contains two particles or contains three particles). In some embodiments, a sample for partitioning further comprises substrates comprising a barcode sequence or repeating clonal barcode sequences as described herein. In some embodiments, a sample for partitioning further comprises one or more additional components, including but not limited to reagents for extension, ligation, reverse transcription, or amplification reactions (e.g., polymerases, nucleotides, buffers, salts, etc.).

Partitions can include any of a number of types of partitions, including solid partitions (e.g., wells or tubes) and fluid partitions (e.g., aqueous droplets within an oil phase). In some embodiments, the partitions are droplets. In some embodiments, the partitions are microchannels. Methods and compositions for partitioning a sample are described, for example, in published patent applications WO 2010/036352, US 2010/0173394, US 2011/0092373, WO 2011/120024, and US 2011/0092376, the entire content of each of which is incorporated by reference herein.

In some embodiments, a sample (e.g., a sample comprising one or more target nucleic acids, particles conjugated to oligonucleotide primers, and/or substrates comprising repeating clonal barcode sequences) is partitioned into a plurality of droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. Methods of emulsion formation are described, for example, in published patent applications WO 2011/109546 and WO 2012/061444, the entire content of each of which is incorporated by reference herein.

In some embodiments, the droplet is formed by flowing an oil phase through an aqueous sample comprising the polynucleotide fragments and ddPCR reaction components. The oil phase may comprise a fluorinated base oil which may additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules may behave as bioreactors able to retain their contents through an incubation period. The conversion to microcapsule form may occur upon heating. For example, such conversion may occur at a temperature of greater than about 40°, 50°, 60°, 70°, 80°, 90°, or 95° C. During the heating process, a fluid or mineral oil overlay may be used to prevent evaporation. Excess continuous phase oil may or may not be removed prior to heating. The biocompatible capsules may be resistant to coalescence and/or flocculation across a wide range of thermal and mechanical processing. Following conversion, the microcapsules may be stored at about −70°, −20°, 0°, 3°, 4°, 5°, 6°, 7°, 8°, 9°, 10°, 15°, 20°, 25°, 30°, 35°, or 40° C.

The microcapsule partitions, which may contain one or more polynucleotide sequences and/or one or more one or more sets of primers pairs, may resist coalescence, particularly at high temperatures. Accordingly, the capsules can be incubated at a very high density (e.g., number of partitions per unit volume). In some embodiments, greater than 100, 000, 500,000, 1,000,000, 1,500,000, 2,000,000, 2,500,000, 5,000,000, or 10,000,000 partitions may be incubated per mL. In some embodiments, the sample-probe incubations occur in a single well, e.g., a well of a microtiter plate, without inter-mixing between partitions. The microcapsules may also contain other components necessary for the incubation.

In some embodiments, a sample (e.g., a sample comprising one or more target nucleic acids, particles conjugated to oligonucleotide primers, and/or substrates comprising a barcode sequence or repeating clonal barcode sequences) is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, a sample (e.g., a sample comprising one or more target nucleic acids, particles conjugated to oligonucleotide primers, and/or substrates comprising a barcode sequence or repeating clonal barcode sequences) is partitioned into a sufficient number of partitions such that at least a majority of partitions have at least about 0.1 but no more than about 10 target nucleic acids per partition (e.g., about 0.1, 0.2, 0.3, 0.4, 0.5, 1, 2, 3, 4, 5, 6, 7, 8, 9, or 10 targets per partition). In some embodiments, at least a majority of the partitions have at least about 0.1 but no more than about 5 targets per partition (e.g., about 0.1, 0.2, 0.3, 0.4, 0.5, 1, 2, 3, 4, or 5 targets per partition). In some embodiments, at least a majority of partitions have no more than about 1 target nucleic acid per partition. In some embodiments, on average about 0.1, 0.2, 0.3, 0.4, 0.5, or 1 target nucleic acids are present in each partition.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL. In some embodiments, the droplets have an average volume of about 50 picoliters to about 2 nanoliters. In some embodiments, the droplets have an average volume of about 0.5 nanoliters to about 50 nanoliters. In some embodiments, the droplets have an average volume of about 0.5 nanoliters to about 2 nanoliters.

Release of Barcode Sequences from Partitions

In some embodiments, after the step of partitioning the sample, particles conjugated to oligonucleotide primers, substrates comprising a barcode sequence or repeating clonal barcode sequences, and/or any other components (e.g., reagents for amplification or polymerization reactions), the individual barcode sequences are released from the substrate comprising the barcode sequence or repeating clonal barcode sequence into the partition. In some embodiments, the step of releasing the barcode sequence or repeating clonal barcode sequences comprises triggering the substrate (e.g., a droplet) to release the plurality of clonal barcode sequences.

In some embodiments, barcode sequences are released from a droplet by breaking the droplet. In some embodiments, heat is used to break the droplet. In some embodiments, a photochemical reaction is used to break the droplet. In some embodiments, acoustic waves are used to break the droplet. In some embodiments, a chemical reaction upon mixing the droplet with the larger partition (e.g., a larger droplet) results in the breaking of the smaller droplet.

In some embodiments, the substrate comprises repeating clonal barcode sequences, and the step of releasing the barcode sequences from the substrate comprises separating the repeating clonal barcode sequence into a plurality of clonal barcode sequences. In some embodiments, the individual clonal barcode sequences are released from a hairpin molecule, linear nucleic acid polymer substrate, or circular nucleic acid polymer substrate by cleaving the hairpin molecule, linear nucleic acid polymer substrate, or circular nucleic acid polymer at the cleavable linker or linkers between the repeating clonal barcode sequences. In some embodiments, the cleavable linker is a restriction enzyme site that is cleaved by a restriction enzyme (e.g., an endonuclease such as a Type II endonuclease or Type IIS endonuclease). For example, in some embodiments, the cleavable linker comprises a Type II restriction enzyme binding site (e.g., HhaI, HindIII, NotI, BbvCI, EcoRI, BglI) or a Type IIS restriction enzyme binding site (e.g., FokI, AlwI, BspMI, MnlI, BbvI, BccI, MboI). In some embodiments, the cleavable linker comprises a uridine incorporated site in a portion of a nucleotide sequence. A uridine incorporated site can be cleaved, for example, using a uracil glycosylase enzyme (e.g., a uracil N-glycosylase enzyme or uracil DNA glycosylase enzyme). In some embodiments, the cleavable linker comprises a photocleavable nucleotide. Photocleavable nucleotides include, for example, photocleavable fluorescent nucleotides and photocleavable biotinylated nucleotides. See, e.g., Li et al., *PNAS,* 2003, 100:414-419; Luo et al., *Methods Enzymol,* 2014, 549:115-131.

Associating Substrate Barcode Sequences with Oligonucleotide Primers on Particles After the substrate barcode sequences are released into the partition, the substrate barcode sequences are associated with particles in the partition in order to generate a nucleic acid signature for the particles in the partition. In some embodiments, a substrate barcode sequence can be associated with two particles located in the same partition, resulting in the virtual joining of the two particles via the substrate barcode sequence. Accordingly, in some embodiments, the method comprises associating a substrate barcode sequence with a first particle conjugated to oligonucleotide primers comprising a first barcode sequence and a second particle conjugated to oligonucleotide primers comprising a second barcode sequence. In some embodiments, wherein the partition comprises three particles, a first substrate barcode sequence can be associated with a first particle conjugated to oligonucleotide primers comprising a first barcode sequence and a second particle conjugated to oligonucleotide primers comprising a second barcode sequence, and a second substrate barcode sequence can be associated with a third particle conjugated to oligonucleotide primers comprising a third barcode sequence.

In some embodiments, the method comprises associating two or more distinct substrate barcode sequences (i.e., a first substrate barcode sequence from a first substrate and a second substrate barcode sequence from a second substrate) with two or more distinct particles conjugated to oligonucleotide primers (e.g., a first particle conjugated to oligonucleotide primers comprising a first barcode sequence, a second particle conjugated to oligonucleotide primers comprising a second barcode sequence, and/or a third particle conjugated to oligonucleotide primers comprising a third barcode sequence). Accordingly, in some embodiments, the associating step comprises associating (1) the first particle conjugated to oligonucleotide primers comprising the first barcode sequence with a first substrate barcode sequence, and (2) the second particle conjugated to oligonucleotide primers comprising the second barcode sequence with a second substrate barcode sequence. In some embodiments, the associating step comprises associating (1) the first particle conjugated to oligonucleotide primers comprising the first barcode sequence with a first substrate barcode sequence; (2) the second particle conjugated to oligonucleotide primers comprising the second barcode sequence with a second substrate barcode sequence; and (3) the third particle conjugated to oligonucleotide primers comprising the third barcode sequence with a third substrate barcode sequence.

In some embodiments, the associating step comprises annealing a substrate barcode sequence (e.g., a clonal barcode sequence) to an oligonucleotide primer conjugated to a particle and extending the annealed products with a polymerase. In some embodiments, the annealing comprises hybridizing a poly-adenine region on a clonal barcode sequence to a poly-thymine region on an oligonucleotide primer conjugated to the particle. See, e.g., FIG. 1. In some embodiments, at least 1, 2, 3, 4, 5, 6, 7, 8, 9, or 10 cycles of annealing and extension are performed to attach the substrate barcode sequences to the oligonucleotide primers. In some embodiments, at least 1 cycle of annealing and extension is performed. In some embodiments, up to 5 cycles or up to 10 cycles of annealing and extension are performed. Annealing and extension methods are described in the art. See, e.g., US 2015/0284712 and US 2015/0322503.

In some embodiments, the associating step comprises hybridizing a clonal barcode sequence to an oligonucleotide primer conjugated to a particle in a partition, then pooling a plurality of partitions and extending the hybridized products with a polymerase in a bulk reaction. Hybridization methods are described in the art. See, e.g., International Application No. PCT/US2015/037525, incorporated by reference herein.

In some embodiments, wherein the substrate comprises a single barcode sequence, the associating step comprises (1) annealing an oligonucleotide primer of the first particle to the substrate barcode sequence and extending the annealed product with a polymerase, and (2) annealing an oligonucleotide primer of the second particle to the substrate barcode sequence and extending the annealed product with the polymerase.

In some embodiments, the extension and amplification reaction comprises the use of a polymerase, e.g., a DNA polymerase. DNA polymerases for use in the methods described herein can be any polymerase capable of replicating a DNA molecule. In some embodiments, the DNA polymerase is a thermostable polymerase. Thermostable polymerases are isolated from a wide variety of thermophilic bacteria, such as *Thermus aquaticus* (Taq), *Pyrococcus furiosus* (Pfu), *Pyrococcus woesei* (Pwo), *Bacillus sterothermophilus* (Bst), *Sulfolobus acidocaldarius* (Sac) *Sulfolobus solfataricus* (Sso), *Pyrodictium occultum* (Poc), *Pyrodictium abyssi* (Pab), and *Methanobacterium thermoautotrophicum* (Mth), as well as other species. DNA polymerases are known in the art and are commercially available. In some embodiments, the DNA polymerase is Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENT™, or an active mutant, variant, or derivative thereof. In some embodiments, the polymerase is Taq DNA polymerase. In some embodiments, the polymerase is a high fidelity DNA polymerase (e.g., iProof™ High-Fidelity DNA Polymerase, Phusion® High-Fidelity DNA polymerase, Q5® High-Fidelity DNA polymerase, Platinum® Taq High Fidelity DNA polymerase, Accura® High-Fidelity Polymerase). In some embodiments, the polymerase is a fast-start polymerase (e.g., FastStart™ Taq DNA polymerase or FastStart™ High Fidelity DNA polymerase). In some embodiments, the polymerase is a strand displacing polymerase (e.g., phi29, or Bst DNA Polymerase, Large Fragment).

In some embodiments, the associating step comprises ligating a substrate barcode sequence (e.g., a clonal barcode sequence) to an oligonucleotide primer of a first particle and to an oligonucleotide primer of a second particle. In some embodiments, the clonal barcode sequence and/or oligonucleotide primer sequence to be annealed are single-stranded nucleic acid. In some embodiments, the ligation reaction comprises the use of a ligase, e.g., a DNA ligase. Exemplary ligases for use in the methods described herein include, but are not limited to, T4 DNA ligase and T4 RNA ligase. Nucleic acid ligation methods are described in the art; see, e.g., Li et al., *Anal Biochem,* 2006, 349:242-246; and Kuhn et al., *FEBS J.,* 2005, 212:5991-6000.

Downstream Applications

Once the particles conjugated to oligonucleotide primers are associated with substrate barcode sequences in order to generate a unique nucleic acid signature for the particles within a specific partition, the nucleic acid signature can be used for deconvoluting data generated in downstream applications, such as downstream detection and/or analysis methods. In some embodiments, the downstream application is sequencing (e.g., high throughput sequencing).

In some embodiments, after the step of associating the substrate barcode sequences with particles in the partition in order to generate a nucleic acid signature for the particles in the partition, the method further comprises associating a target nucleic acid in the partition with a particle in the partition. In some embodiments, the step of associating a target nucleic acid in the partition with a particle in the partition comprises hybridizing a target nucleic acid, or a portion thereof, to a portion of an oligonucleotide primer conjugated to a particle. In some embodiments, the target nucleic acid or portion thereof hybridizes to a universal tag portion or to a random sequence portion of the oligonucleotide primer.

In some embodiments, the step of associating a target nucleic acid in a partition with a particle in the partition is carried out prior to the step of associating the substrate barcode sequences with particles in the partition. In some embodiments, while in partition, a target nucleic acid or a portion thereof is hybridized to a portion of an oligonucleotide primer conjugated to a particle, and the clonal barcode sequence is also hybridized to a portion of the oligonucleotide primer conjugated to the particle. The partitions are then broken and the contents of multiple partitions are pooled before performing an extension reaction to extend the hybridized target nucleic acid-oligonucleotide primer product and the hybridized substrate barcode sequence-oligonucleotide primer product.

In some embodiments, the method further comprises polymerizing the hybridized target nucleic acid-oligonucleotide primer product. In some embodiments, the polymerization comprises primer extension. In some embodiments, the polymerization comprises reverse transcription (e.g., reverse transcription of a RNA target nucleic acid). In some embodiments, the method further comprises amplifying the target nucleic acid-oligonucleotide primer product. In some embodiments, the amplification reaction is a droplet digital PCR reaction. Methods for performing PCR in droplets are described, for example, in US 2014/0162266, US 2014/0302503, and US 2015/0031034, the contents of each of which is incorporated by reference.

Release of Partition Contents

In some embodiments, after the particles conjugated to oligonucleotide primers are associated with substrate barcode sequences in order to generate a unique nucleic acid signature for each partition, the contents of the partitions (e.g., target nucleic acids associated with a particle as described herein) are released prior to the downstream application, e.g., to pool multiple partitions for a downstream application such as a sequencing reaction. Partition breaking can be accomplished by any of a number of methods, including but not limited to electrical methods and introduction of a destabilizing fluid. See, e.g., Zeng et al., *Anal Chem* 2011, 83:2083-2089. Methods of breaking partitions are also described, for example, in US 2013/0189700, incorporated by reference herein.

In some embodiments, partitions are broken by mixing the partitions (e.g., droplets) with a destabilizing fluid. In some embodiments, the destabilizing fluid is chloroform. In some embodiments, the destabilizing fluid comprises a perfluorinated alcohol. In some embodiments, the destabilizing fluid comprises a fluorinated oil, such as a perfluorocarbon oil.

In some embodiments, the method further comprises purifying a target nucleic acid that is released from a partition (e.g., a target nucleic acid associated with a particle as described herein), e.g., in order to separate the target nucleic acid from other partition components. In some embodiments, the purifying step comprises the use of solid-phase reversible immobilization (SPRI) paramagnetic bead reagents. SPRI paramagnetic bead reagents are commercially available, for example in the Agencourt AMPure XP PCR purification system (Beckman-Coulter, Brea, Calif.).

Sequencing

In some embodiments, a target nucleic acid from a partition having a unique nucleic acid signature as described herein is analyzed by a sequencing or genotyping method. In some embodiments, the target nucleic acid is analyzed by sequencing, e.g., high throughput sequencing. In some embodiments, the method of analyzing a partitioned sample (e.g., a cell or target nucleic acid) further comprises determining the nucleic acid signatures of sequence reads and deconvoluting the nucleic acid signatures in order to allow sequence information from each partitioned sample to be uniquely identified.

Methods for high throughput sequencing and genotyping are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety.

Exemplary DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No. WO 2006/084,132, herein incorporated by reference in its entirety). In some embodiments, DNA sequencing is achieved by parallel oligonucleotide extension (See, e.g., U.S. Pat. Nos. 5,750,341; and 6,306,597, both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511,803; herein incorporated by reference in their entireties), the 454 picotiter pyrosequencing technology (Margulies et al., 2005 Nature 437, 376-380; U.S. Publication No. 2005/0130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbial., 7:287-296; U.S. Pat. Nos. 6,210,891; and 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55. 641-658, 2009; MacLean et al., Nature Rev. Microbial., 7:287-296; U.S. Pat. Nos. 6,833,246; 7,115,400; and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbial., 7:287-296; U.S. Pat. Nos. 5,912,148; and 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In some embodiments, nanopore sequencing is employed (See, e.g., Astier et al., J. Am. Chem. Soc. 2006 Feb. 8; 128(5)1705-10, incorporated by reference). The theory behind nanopore sequencing relates to what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In some embodiments, HeliScope by Helicos BioSciences is employed (Voelkerding et al., Clinical Chem., 55. 641-658, 2009; MacLean et al., Nature Rev. Microbial, 7:287-296; U.S. Pat. Nos. 7,169,560; 7,282,337; 7,482,120; 7,501,245; 6,818,395; 6,911,345; and 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (See, e.g., Science 327 (5970): 1190 (2010); U.S. Pat. Appl. Pub. Nos. 2009/0026082; 2009/0127589; 2010/0301398; 2010/0197507; 2010/0188073; and 2010/0137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 2009/0035777, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; and U.S. patent application Ser. No. 11/671,956; and Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., Clinical Chem., 55. 641-658, 2009; MacLean et al., Nature Rev. Microbiol., 7:287-296; U.S. Pat. Nos. 7,170,050; 7,302,146; 7,313,308; and 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In some embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. Nos. 7,405,281; 7,315,019; 7,313,308; 7,302,146; and 7,170,050; and U.S. Pat. Pub. Nos. 2008/0212960; 2008/0206764; 2008/0199932; 2008/0199874; 2008/0176769; 2008/0176316; 2008/0176241; 2008/0165346; 2008/0160531; 2008/0157005; 2008/0153100; 2008/0153095; 2008/0152281; 2008/0152280; 2008/0145278; 2008/0128627; 2008/0108082; 2008/0095488; 2008/0080059; 2008/0050747; 2008/0032301; 2008/0030628; 2008/0009007; 2007/0238679; 2007/0231804; 2007/0206187; 2007/0196846; 2007/0188750; 2007/0161017; 2007/0141598; 2007/0134128; 2007/0128133; 2007/0077564; 2007/0072196; and 2007/0036511; and Korlach et al. (2008), "Selective aluminum passivation for targeted immobilization of single DNA polymerase molecules in zero-mode waveguide nanostructures," *PNAS* 105(4): 1176-81, all of which are herein incorporated by reference in their entireties.

III. Partition Libraries

In another aspect, partition libraries comprising a plurality of partitions (e.g., at least about 100; 200; 300; 500; 750; 1000; 2500; 5000; 7500; 10,000; 15,000; 20,000; 30,000, or more partitions) are provided. In some embodiments, at least some partitions comprise at least a first particle conjugated to oligonucleotide primers comprising a first barcode sequence and a second particle conjugated to oligonucleotide primers comprising a second barcode sequence. In some embodiments, the partitions comprise 0, 1, or more than 1 particles per partition. In some embodiments, the partitions have an average of about one particle per partition. In some embodiments, the partitions have an average of about two particles per partition. In some embodiments, the partitions have an average of about three particles per partition.

In some embodiments, at least some partitions of the partition library (e.g., a majority, substantially all, or all of the partitions of the partition library) comprise at least a first particle conjugated to oligonucleotide primers comprising a first barcode sequence and a second particle conjugated to oligonucleotide primers comprising a second barcode sequence, and further comprise a substrate comprising a barcode sequence or repeating clonal barcode sequences. In some embodiments, at least some partitions of the partition library comprise (1) two particles, wherein the first particle is conjugated to oligonucleotide primers comprising a first barcode sequence and the second particle conjugated to oligonucleotide primers comprising a second barcode sequence; and (2) a substrate comprising a barcode sequence or repeating clonal barcode sequences. In some embodiments, at least some partitions of the partition library comprise (1) three particles, wherein the first particle is conjugated to oligonucleotide primers comprising a first barcode sequence, the second particle conjugated to oligonucleotide primers comprising a second barcode sequence, and the third particle is conjugated to oligonucleotide primers comprising a third barcode sequence; and (2) at least two substrates, each comprising a barcode sequence or repeating clonal barcode sequences, wherein the barcode sequences of the first substrate and the second substrate are distinguishable sequences. In some embodiments, a majority, substantially all, or all of the partitions of the partition library comprise at least one particles, at least two particles, or at least three particles. Particles having conjugated to oligonucleotide primers conjugated thereto and substrates comprising the barcode sequences or repeating clonal barcode sequences are described in Section II above.

In some embodiments, at least some partitions of the partition library comprise at least a first particle conjugated to oligonucleotide primers comprising a first barcode sequence and a second particle conjugated to oligonucleotide primers comprising a second barcode sequence, and at least one substrate barcode sequence associated with the first particle and the second particle. In some embodiments, at least some partitions of the partition library comprise (1) a first particle conjugated to oligonucleotide primers comprising a first barcode sequence with a first substrate barcode sequence, and (2) a second particle conjugated to oligonucleotide primers comprising a second barcode sequence with a second substrate barcode sequence. In some embodiments, a majority, substantially all, or all of the partitions of the partition library comprise at least two particles. In some embodiments, the first substrate barcode sequence and the second substrate barcode sequence are distinguishable sequences. In some embodiments, the first substrate barcode sequence and the second substrate barcode sequence are identical sequences. In some embodiments, the substrate barcode sequences are contiguity preserved tagmented polynucleotide (e.g., DNA) sequences.

In some embodiments, at least some partitions of the partition library (e.g., a majority, substantially all, or all of the partitions of the partition library) comprise (1) a first particle conjugated to oligonucleotide primers comprising a first barcode sequence with a first substrate barcode sequence; (2) a second particle conjugated to oligonucleotide primers comprising a second barcode sequence with a second substrate barcode sequence; and (3) a third particle conjugated to oligonucleotide primers comprising a third barcode sequence with a third substrate barcode sequence. In some embodiments, a majority, substantially all, or all of the partitions of the partition library comprise at least three particles.

In some embodiments, the substrate comprises repeating clonal barcode sequences. In some embodiments, the repeating clonal barcode sequences comprise tandem repeating clonal barcode sequences that are separated by a cleavable linker (e.g., a hairpin molecule, a linear nucleic acid polymer, or a circular nucleic acid polymer as described herein). In some embodiments, the substrate comprising the barcode sequence or repeating clonal barcode sequences is a droplet encapsulating the barcode sequence or repeating clonal barcode sequences.

In some embodiments, at least some partitions of the partition library (e.g., a majority, substantially all, or all of the partitions of the partition library) further comprise a sample (e.g., one or more target nucleic acids, or one or more cells). In some embodiments, the sample comprising target nucleic acids comprises DNA, RNA, or a combination or hybrid thereof. In some embodiments, the sample is a sample comprising cells, e.g., is a single-cell sample. In some embodiments, the sample is a sample as described in Section II above.

In some embodiments, the partitions further comprise additional reagents or components for polymerization, amplification, reverse transcription, or primer extension (e.g., polymerases, salts, nucleotides, buffers, stabilizers, primers, detectable agents, or nuclease-free water) as described herein.

IV. Kits

In another aspect, kits for generating a nucleic acid signature for identifying particles associated in a partition are provided. In some embodiments, a kit comprises:
(a) a plurality of particles comprising a solid support surface, the solid support surface of a particle having a plurality of oligonucleotide primers conjugated thereon, wherein the oligonucleotide primers comprise a barcode sequence and wherein at least a majority of the plurality of oligonucleotide primers conjugated to a solid support surface comprise the same barcode sequence; and
(b) a substrate comprising a barcode sequence or repeating clonal barcode sequences.

Particles having conjugated to oligonucleotide primers conjugated thereto and substrates comprising the barcode sequence or repeating clonal barcode sequences are described in Section II above.

In some embodiments, the substrate comprises repeating clonal barcode sequences that comprise tandem repeating clonal barcode sequences that are separated by a cleavable linker (e.g., a hairpin molecule, a linear nucleic acid polymer, or a circular nucleic acid polymer as described herein). In some embodiments, the substrate comprising the barcode sequence or repeating clonal barcode sequences is a droplet encapsulating the repeating clonal barcode sequences.

In some embodiments, the kit further comprises one or more reagents for polymerization, amplification, reverse transcription, or primer extension (e.g., polymerases, salts, nucleotides, buffers, stabilizers, primers, detectable agents, or nuclease-free water) as described herein.

In some embodiments, the kit further comprises instructions for performing a method as described herein (e.g., instructions for partitioning or instructions for associating substrate barcode sequences with particles conjugated to oligonucleotide primers).

VI. Examples

The following examples are offered to illustrate, but not to limit, the claimed invention.

Example 1: Generation of Nucleic Acid Sequence for Virtually Linking Oligonucleotide-Loaded Beads in Partitions In partition libraries that are not loaded with beads (such as oligonucleotide-loaded beads) in a deterministic fashion, bead concentrations are typically adjusted so that only about 1 out of 10 partitions are occupied by a bead, in order to ensure that partitions have only 1 bead. This results in about 90% dead volume in the partitions.

If bead concentration is adjusted resulting in either 2 or 3 beads per partition on average, droplet occupancy increases to 85% and 95%, respectively. One benefit of such an approach is that dead volume is drastically minimized. In such a high occupancy scheme, with oligonucleotide-loaded beads present at 1×-4× concentrations, very little detrimental effect is expected on molecular biology reactions (e.g., a reverse transcription reaction). However, it would be beneficial to be able to deconvolute which beads are present together in a single partition (e.g., for deconvoluting sequencing data).

One approach for deconvoluting which beads are present together in a single partition is to provide partitions with substrates comprising barcode sequences for generating a unique combination of sequences for beads in a particular partition, such that upon their sequence analysis (e.g., by next-generation sequencing), the beads are virtually linked. An exemplary schematic of such an approach is shown in FIG. 1. As shown in FIG. 1, partitions (e.g., droplets) are loaded to have on average 2 barcode-labeled oligonucleotide-loaded beads, resulting in 85% droplet occupancy. Droplets are also loaded with substrates comprising repeating clonal barcode sequences (as shown in FIG. 1A, hairpin substrates), for example at a concentration of about 100-200 hairpin substrates per droplet to ensure that each droplet is provided with sufficient hairpin substrates for attaching to the oligonucleotides of beads. For releasing the clonal barcode sequences into separate sequences, the linkers in the hairpins are cleaved. The separated clonal barcode sequences are denatured into single-stranded sequences, and then annealing and extension are carried out to attach the clonal barcode sequences to the oligonucleotides of the beads, thus creating unique combinations of barcode-labeled oligonucleotide-loaded beads and clonal barcode sequences. For example, as shown in FIG. 1C, by seeing that both beads 1 and 2 are joined with clonal barcode sequence 5, one can deconvolute that both beads occupied the same droplet.

Figure 3:
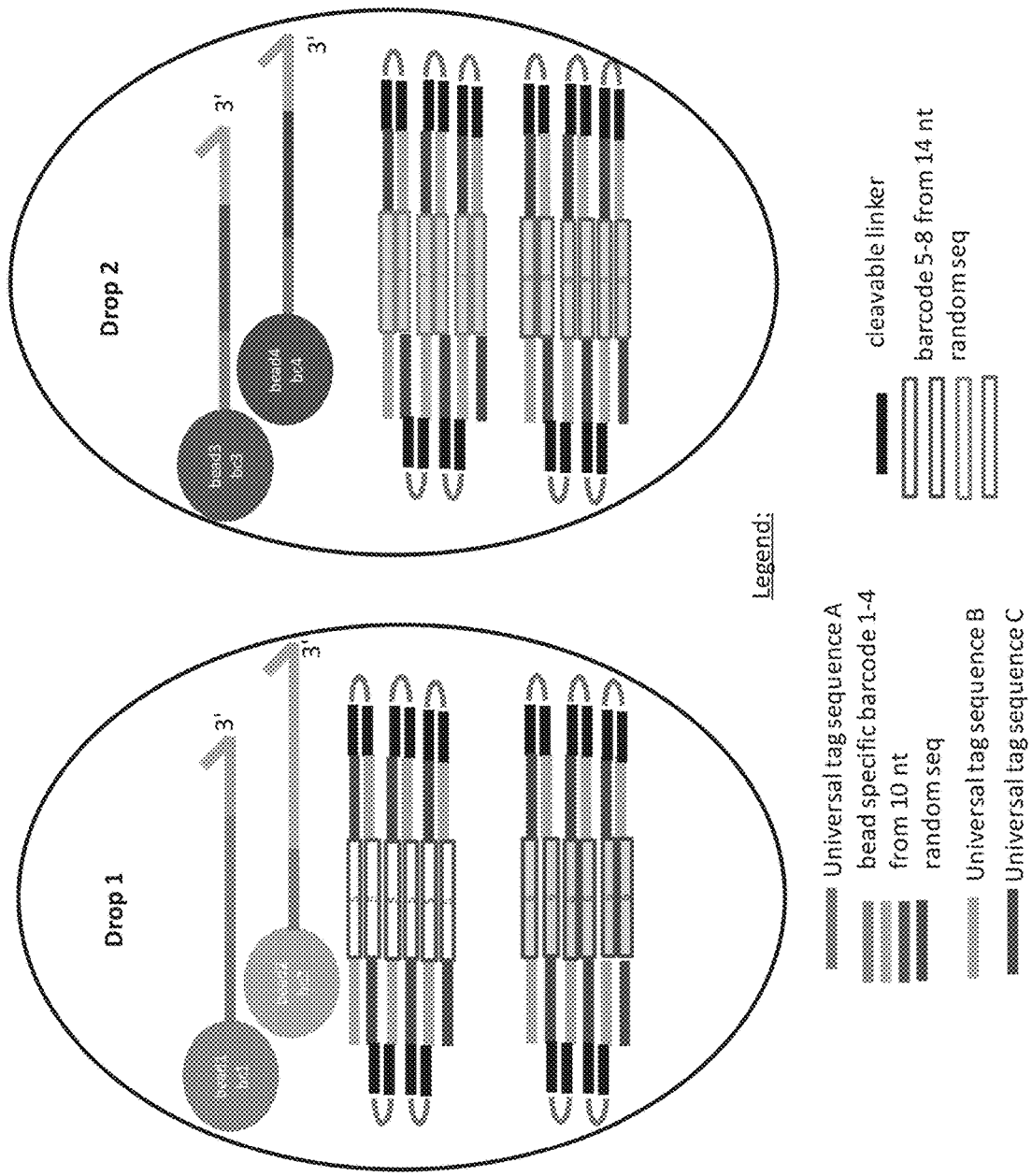
FIG. 3. Substrates comprising repeating clonal barcode sequences can be linear substrates, including single stranded nucleic acid polymers (RNA, DNA, or a mixture thereof) and double stranded nucleic acid polymers (RNA, DNA, or a mixture thereof).

As shown in FIG. 2 and FIG. 3, a similar strategy of combining oligonucleotides on beads and clonal barcode sequences can be carried out using clonal barcode substrates that are circular substrates (FIG. 2) or linear substrates (FIG. 3), including single stranded nucleic acid polymers (RNA, DNA, or a mixture thereof) and double stranded nucleic acid polymers (RNA, DNA, or a mixture thereof).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of generating a nucleic acid signature for identifying particles associated in a partition, the method comprising:
(a) partitioning a sample into a plurality of partitions, each partition comprising a particle comprising a solid support surface, the solid support surface having a plurality of oligonucleotide primers conjugated thereon, wherein the oligonucleotide primers comprise a barcode sequence that is unique to the particle and wherein at least a majority of the plurality of oligonucleotide primers conjugated to a solid support surface comprise the same barcode sequence;
(b) providing in the partitions of step (a) one or more barcode sequences that are from a substrate comprising a barcode sequence or repeating clonal barcode sequences, wherein the barcode sequence or repeating clonal barcode sequences of the substrate comprise a region of nucleotide sequence that is a unique identifier sequence for the barcode sequence(s) from the substrate; and
(c) for a partition from step (b) that comprises more than one particle, generating a nucleic acid signature for the particles in the partition by attaching different clonal copies of the barcode sequences from the substrate to (i) an oligonucleotide primer comprising a first barcode sequence that is conjugated to a first particle and (ii) an oligonucleotide primer comprising a second barcode sequence that is conjugated to a second particle;
thereby generating a nucleic acid signature for the particles that are in the partition.

2. The method of claim 1, wherein step (b) comprises releasing the barcode sequence or the repeating clonal barcode sequences from the substrate.

3. The method of claim 2, wherein the substrate comprises tandem repeating clonal barcode sequences that are separated by a cleavable linker, and wherein the releasing comprises cleaving the substrate at the cleavable linker.

4. The method of claim 2, wherein the substrate comprising the barcode sequence or the repeating clonal barcode sequences comprises a droplet encapsulating the barcode sequence or repeating clonal barcode sequences, and wherein the releasing comprises breaking the droplet.

5. The method of claim 1, wherein the substrate barcode sequence or repeating clonal barcode sequences comprise DNA, RNA, or a DNA/RNA hybrid.

6. The method of claim 1, wherein the substrate barcode sequence is a contiguity preserved tagmented polynucleotide sequence.

7. The method of claim 1, wherein the substrate comprises repeating clonal barcode sequences.

8. The method of claim 7, wherein the substrate comprising the repeating clonal barcode sequences is a hairpin molecule.

9. The method of claim 7, wherein the substrate comprising the repeating clonal barcode sequences is a linear polynucleotide substrate.

10. The method of claim 7, wherein the substrate comprising the repeating clonal barcode sequences is a circular polynucleotide substrate.

11. The method of claim 7, wherein the repeating clonal barcode sequences comprise at least 10 repeats of the clonal barcode sequence.

12. The method of claim 1, wherein the barcode sequence or repeating clonal barcode sequence of the substrate has a length of at least 6 nucleotides.

13. The method of claim 1, wherein the substrate comprises a single barcode sequence, and wherein step (c) comprises: (1) annealing an oligonucleotide primer of the first particle to the substrate barcode sequence and extending the annealed product with a polymerase, and (2) annealing an oligonucleotide primer of the second particle to the substrate barcode sequence and extending the annealed product with the polymerase.

14. The method of claim 1, wherein in step (b), a plurality of substrates comprising a barcode sequence or repeating clonal barcode sequences are provided to the partition, wherein the plurality of substrates comprise distinguishable barcode sequences.

15. The method of claim 1, wherein the partitions have an average of at least two particles per partition.

16. The method of claim 1, wherein step (c) comprises annealing the first substrate barcode sequence to an oligonucleotide primer of the first particle and the second substrate barcode sequence to an oligonucleotide primer of the second particle and extending the annealed products with a polymerase.

17. The method of claim 1, wherein step (c) comprises ligating a substrate barcode sequence to both an oligonucleotide primer of the first particle and an oligonucleotide primer of the second particle.

18. The method of claim 1, wherein the partitions are droplets.

* * * * *